(12) United States Patent
Lievois et al.

(10) Patent No.: US 8,569,686 B2
(45) Date of Patent: Oct. 29, 2013

(54) MULTI-CHANNEL INFRARED OPTICAL PHASE FRACTION METER

(71) Applicant: Weatherford/Lamb, Inc., Houston, TX (US)

(72) Inventors: John Lievois, Houston, TX (US); David Atkinson, Spring, TX (US)

(73) Assignee: Weatherford/Lamb, Inc., Houston, TX (US)

( * ) Notice: Subject to any disclaimer, the term of this patent is extended or adjusted under 35 U.S.C. 154(b) by 0 days.

(21) Appl. No.: 13/761,953

(22) Filed: Feb. 7, 2013

(65) Prior Publication Data

US 2013/0146757 A1    Jun. 13, 2013

Related U.S. Application Data

(60) Division of application No. 11/764,658, filed on Jun. 18, 2007, which is a continuation of application No. 11/065,489, filed on Feb. 24, 2005, now Pat. No. 7,233,001.

(51) Int. Cl.
*G01V 5/08* (2006.01)
*G01J 5/02* (2006.01)
*G01F 1/00* (2006.01)

(52) U.S. Cl.
USPC .................. 250/269.1; 225/356.1; 225/339.12

(58) Field of Classification Search
USPC .................. 250/269.1, 356.1, 339.12
See application file for complete search history.

(56) References Cited

U.S. PATENT DOCUMENTS

| 4,228,353 A | * | 10/1980 | Johnson ................ 250/356.1 |
| 4,994,671 A | * | 2/1991 | Safinya et al. .......... 250/255 |
| 5,276,327 A | | 1/1994 | Bossen et al. |
| 5,331,156 A | | 7/1994 | Hines |
| 5,654,551 A | * | 8/1997 | Watt et al. ................ 250/356.1 |
| 5,729,013 A | | 3/1998 | Bergren, III |

(Continued)

FOREIGN PATENT DOCUMENTS

| JP | 09318526 | 12/1997 |
| WO | 2004095010 | 11/2004 |

OTHER PUBLICATIONS

Preliminary Examination and Search Report dated Jun. 30, 2006, issued by the European Patent Office in Application No. GB0603842.6.

(Continued)

*Primary Examiner* — David Porta
*Assistant Examiner* — Mindy Vu
(74) *Attorney, Agent, or Firm* — Patterson & Sheridan, LLP

(57) ABSTRACT

Methods and apparatus for measuring a phase fraction of a flow stream are disclosed. An infrared phase fraction meter includes a light source for emitting into a flow stream infrared radiation that includes first and second wavelength bands. The first wavelength band substantially transmits through first and second phases of the flow stream and is substantially absorbed by a third phase. In contrast, the second wavelength band is substantially absorbed by the second phase relative to the first and third phases. One or more detectors simultaneously detect attenuation of the first and second wavelength bands upon the infrared radiation passing through at least a portion of the flow stream, and a phase fraction of the second phase is determined based on the attenuation. As an example, the first, second and third phases are gas, water and oil, respectively, produced from a well.

20 Claims, 5 Drawing Sheets

(56) References Cited

U.S. PATENT DOCUMENTS

| | | |
|---|---|---|
| 6,076,049 A | 6/2000 | Lievois |
| 6,292,756 B1 | 9/2001 | Lievois |
| 6,343,507 B1 * | 2/2002 | Felling et al. .............. 73/152.19 |
| 6,678,050 B2 * | 1/2004 | Pope et al. .................... 356/435 |
| 7,233,001 B2 | 6/2007 | Lievois |
| 2003/0056581 A1 | 3/2003 | Turner |
| 2004/0069942 A1 | 4/2004 | Fujisawa |
| 2005/0094921 A1 | 5/2005 | DiFoggio |
| 2006/0092423 A1 | 5/2006 | Servaites |

OTHER PUBLICATIONS

Office Action dated Apr. 9, 2013, issued by the Canadian Intellectual Property Office in corresponding Application No. 2,673,783.

* cited by examiner

MULTI-CHANNEL INFRARED OPTICAL PHASE FRACTION METER

CROSS-REFERENCE TO RELATED APPLICATIONS

This is a divisional of U.S. patent application Ser. No. 11/764,658 filed Jun. 18, 2007, which is a continuation of U.S. patent application Ser. No. 11/065,489 filed Feb. 24, 2005, now U.S. Pat. No. 7,233,001, both of which are incorporated by reference.

BACKGROUND OF THE INVENTION

1. Field of the Invention

Embodiments of the invention generally relate to phase fraction meters such as water cut meters, and more particularly to an infrared optical phase fraction meter.

2. Description of the Related Art

Oil and gas wells often produce water along with hydrocarbons during normal production from a hydrocarbon reservoir within the earth. The water resident in the reservoir frequently accompanies the oil and/or gas as it flows up to surface production equipment. Operators periodically measure the fractions of an overall production flow stream that are water/oil/gas for purposes such as improving well production, allocating royalties, properly inhibiting corrosion based on the amount of water and generally determining the well's performance.

In many cases, several wells connect to a manifold in order to selectively isolate one of the wells and measure phase fractions of the production flow from that well. The manifold enables the flow from the well isolated from the combined flow to be diverted and either measured with a phase fraction meter without separation or sent to a separator where the individual production of oil, water, and gas are subsequently measured. In some cases, two phase separators divide the gas from the combined oil and water stream. In this scenario, flow meters measure the gas stream and the combined liquid production stream. In addition, the operator must obtain the percentages of the oil and water in the combined liquid stream to determine net oil and water production. This typically requires the time-consuming and expensive process of manual sampling or the use of an online device called a water cut meter.

As an alternative to the two phase separator, a three phase separator isolates the gas, oil and water so each phase can be metered independently. However, the three phase separator occupies a considerably larger space than the simpler two phase separators and is more expensive to own and operate. Further, inefficient separation or the propensity of certain oils to bind water in a tight emulsion still necessitates manual sampling in the oil and water legs.

Conventional water cut meters include capacitive water cut meters, density water cut meters, and microwave water cut meters. However, capacitive, density and microwave water cut meters each possess particular limitations. In general, these limitations include detection of oil-water concentrations only within a limited range, calibration difficulties, high costs, and results affected by the presence of gas bubbles, salinity fluctuations and density changes or close densities of oil and water.

Additionally, various infrared optical sensors enable water cut measurements. These infrared optical sensors overcome some of the limitations associated with other types of water cut meters. However, problems such as non-absorbance based signal attenuation and low water cuts can prevent accurate measurements using the infrared optical sensors.

Thus, there exists a need for an improved phase fraction meter. There exists a further need for an infrared optical phase fraction meter that minimizes measurement errors and enables accurate measurement across a full range of water cut. A still further need exists for an infrared optical phase fraction meter capable of measuring a water/oil ratio even in the presence of small levels of a third phase such as a free gas.

SUMMARY OF THE INVENTION

Embodiments of the invention generally relate to methods and apparatus for measuring a phase fraction of a flow stream. According to some embodiments, an infrared phase fraction meter includes a light source for emitting into a flow stream infrared radiation that includes first second, third, and fourth wavelength bands. One wavelength is predominantly an oil absorber, one is predominantly a water absorber, one is predominantly a reference and the fourth is an extra. The extra may be used as a second oil absorber to improve performance over a wide range of oil types. While only a difference in absorption at one wavelength for two of the three phase fractions (nominally water and oil) is required, the additional wavelength bands improve accuracy and/or range of operating conditions. In some applications, two or three wavelength bands suffice, and the other channels are not populated to save costs. The first wavelength band substantially transmits through first and second phases of the flow stream and is substantially absorbed by a third phase. In contrast, the second wavelength band is substantially absorbed by the second phase relative to the first and third phases. One or more detectors simultaneously detect attenuation of the first and second wavelength bands upon the infrared radiation passing through at least a portion of the flow stream, and a phase fraction of the second phase is determined based on the attenuation. As an example, the first, second and third phases are gas, water and oil, respectively, produced from a well.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 3A is an end view of a connector taken across line 3A-3A in FIG. 3.

DETAILED DESCRIPTION

Embodiments of the invention generally relate to phase fraction meters that utilize infrared optical analysis techniques. While the phase fraction meter is illustrated as part of a test system that detects phase fractions from a flow stream being produced from a well, use of the phase fraction meter includes various other applications. For example, the phase fraction meter can be used to monitor flows associated with an overboard discharge treatment facility that treats the water produced from the well prior to its discharge into an ocean. Additionally, other industries such as pharmaceutical, food, refinery, chemical, paper, pulp, petroleum, gas, mining, minerals and other fluid processing plants often utilize phase fraction meters in order to detect such aspects as water content.

Figure 1:
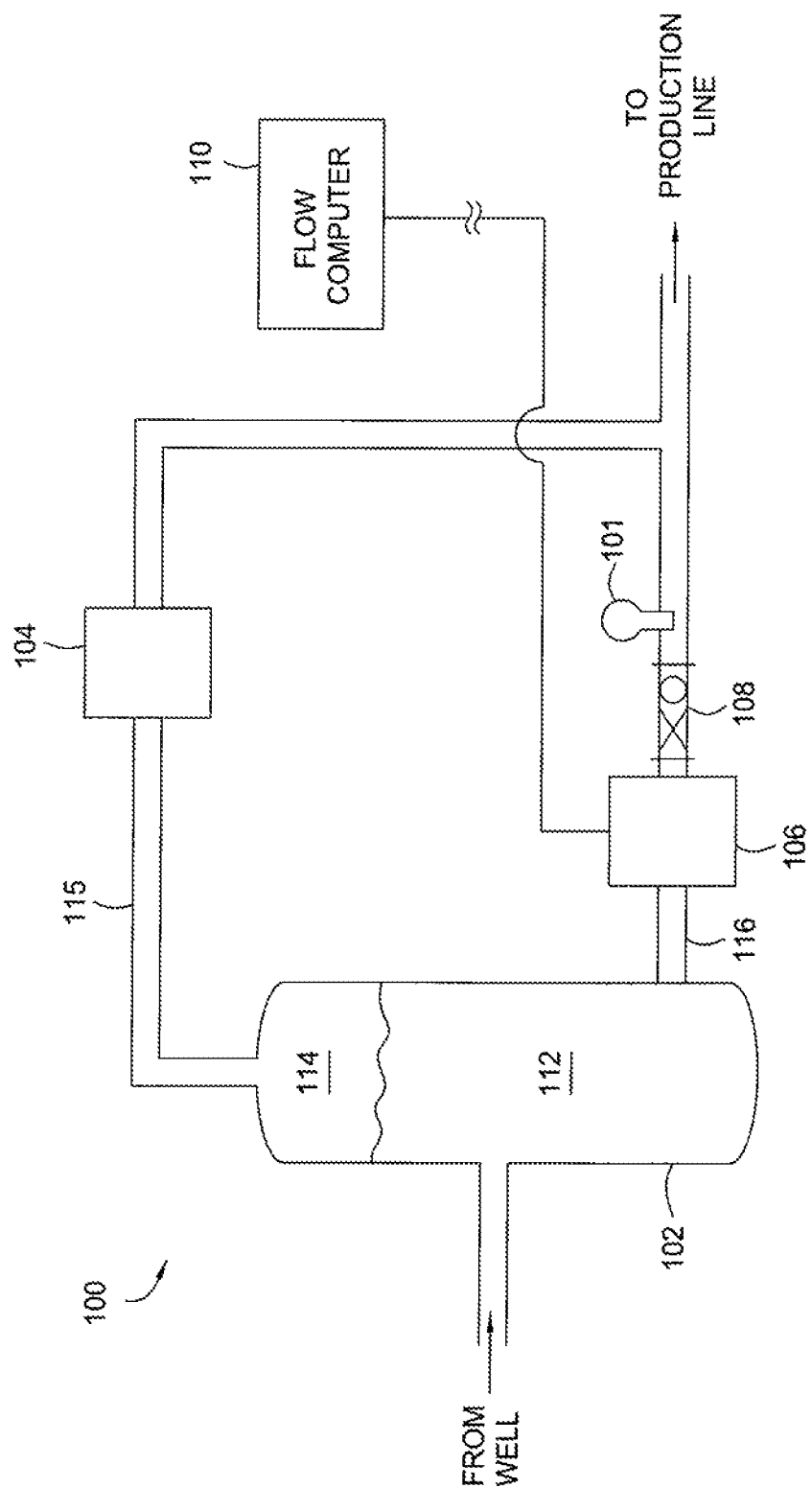
FIG. 1 is a schematic diagram of a well testing system that includes an infrared phase fraction meter in accordance with embodiments of the invention.

FIG. 1 shows a well testing system 100 including an infrared phase fraction meter 101 in accordance with embodiments of the invention. U.S. Pat. Nos. 6,076,049 and 6,292,756, which are herein incorporated in their entirety, further describe examples of infrared water fraction systems such as the testing system 100. The well testing system 100 takes a production flow directly from a well or from a common gathering station (not shown) that provides a manifold to direct one well at a time to the testing system 100 while production from a plurality of other wells is directed to a production line by bypassing the testing system 100. The testing system 100 includes a separator 102, a gas flow meter 104, a liquid flow meter 106, an optional mixer 108, the infrared phase fraction meter 101 and a flow computer 110. For some embodiments and applications, the separator 102 and the gas flow meter 104 may not be required as will be apparent from the following discussion. The separator 102 divides the production flow into a liquid portion 112 that includes water content and oil content of the production flow and a gas portion 114 that includes gas content of the production flow.

The gas flow meter 104 measures flow through a gas stream 115. On the other hand, a flow stream 116 passes from the liquid portion 112 of the separator 102 to the liquid flow meter 106 and the infrared phase fraction meter 101. The flow stream 116 often includes some gases even after being separated and may even be a fluid stream that has not been separated. The liquid flow meter 106 detects an overall flow rate of the flow stream 116 without differentiating phases making up the flow stream 116. Accordingly, determining a flow rate of individual phases requires determining what percent of the flow stream 116 that each phase makes up. In one embodiment, the infrared phase fraction meter 101 detects a water cut of the flow stream 116. Thus, the phase fraction meter 101 along with the liquid flow meter 106 enables calculation of the flow rate of water and oil phases.

In general, the mixer 108 includes any structure or device capable of making the flow stream 116 more homogenous prior to being sampled by the infrared phase fraction meter 101. For example, a set of axially spaced veins or blades disposed within a flow path of the flow stream 116 forms a static mixer for use as the mixer 108. The phase fraction meter 101 may not require incorporation of the mixer 108 within the flow stream 116 as would be the case when the flow stream 116 is sufficiently mixed.

Figure 2:
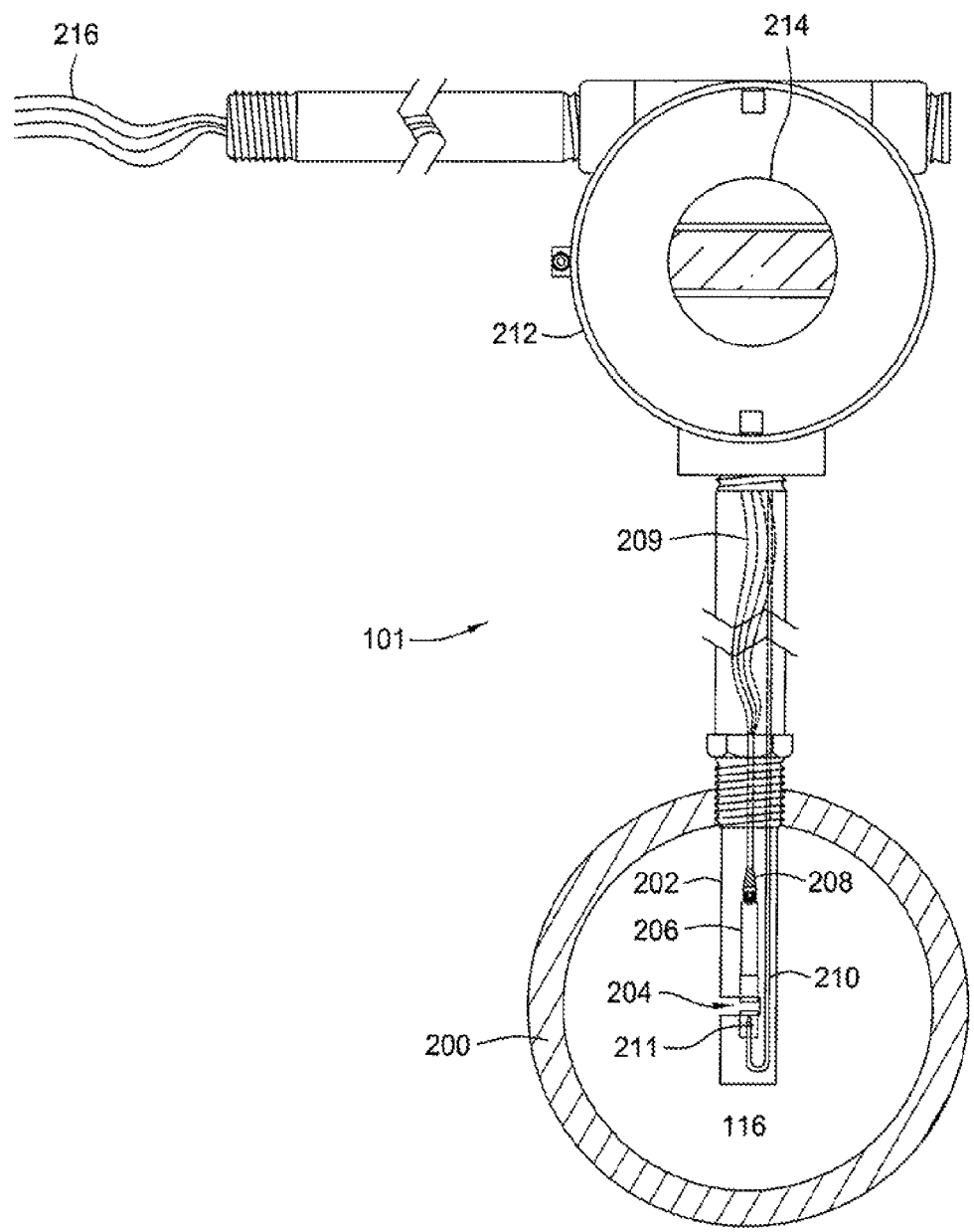
FIG. 2 is a partial section view of an infrared phase fraction meter having a probe end inserted into a pipe.

FIG. 2 illustrates the phase fraction meter 101 disposed on a pipe 200 that carries the flow stream 116 therein. A probe end 202 of the meter 101 inserts into the pipe 200 such that a sampling region 204 is preferably located in a central section of the pipe 200. A body portion 212 of the meter 101 couples to the probe end 202 and houses electronics (not shown) and an optional local display 214 outside of the pipe 200. The meter 101 further includes a broad band infrared source 211 coupled to a power supply line 210 and located on an opposite side of the sampling region 204 from a collimator 206 that is coupled to the body portion 212 by optical outputs 209 connected thereto by a common connector 208 such as a Sub-Miniature Version A (SMA) connector. For some embodiments, the source 211 includes a tungsten halogen lamp capable of emitting light in a range of wavelengths that includes particular wavelengths selected for interrogation as discussed in detail below. Input and output wiring connections 216 lead from the body portion 212 of the meter 101 for providing power to the meter 101 and communication with the flow computer 110 (shown in FIG. 1) and optionally the liquid flow meter 106 (shown in FIG. 1). When the phase fraction meter 101 is connected to the flow meter 106, the phase fraction meter 101 may capture flow data from the flow meter 106 as a 4-20 milliamp or frequency based signal that can be processed and made accessible to the flow computer 110, for example, via the wiring connections 216 using an industry standard protocol, such as Modbus.

Figure 3:
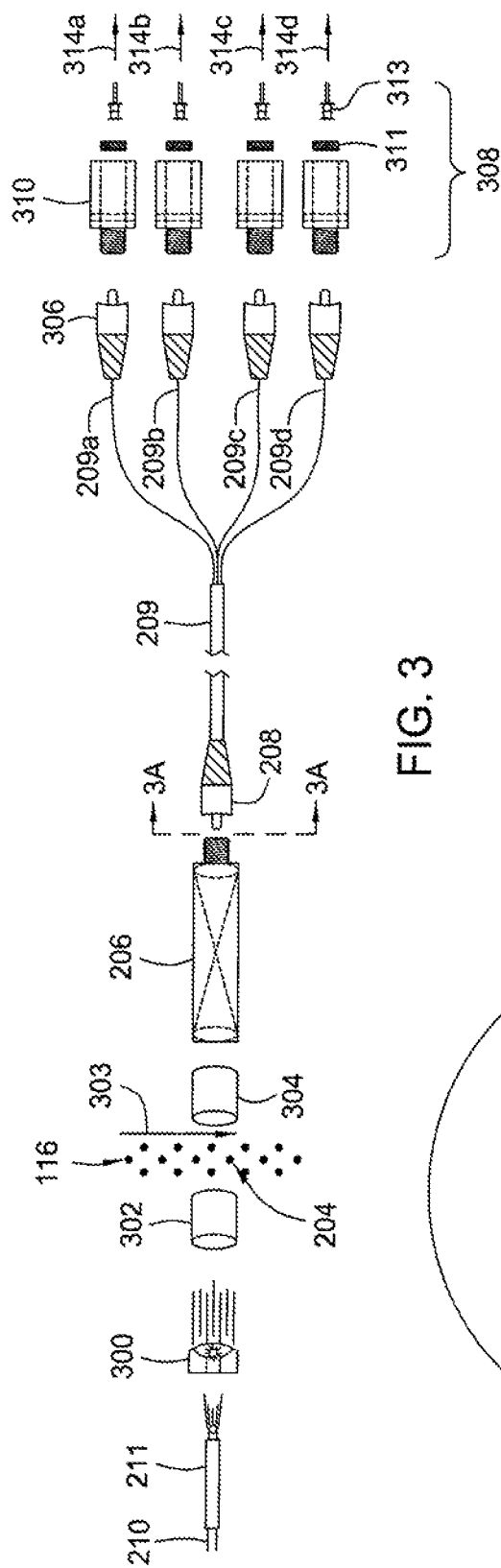
FIG. 3 is an exploded view of internal components of the infrared phase fraction meter illustrated in FIG. 2.

FIG. 3 illustrates internal components of the infrared phase fraction meter 101 in an exploded view. These components include the source 211, a parabolic reflector 300 for directing light from the source 211, first and second sapphire plugs 302, 304, the collimator 206 and the optical outputs 209 that couple the collimator 206 to infrared filters 308. An area between the sapphire plugs 302, 304 defines the sampling region 204 where fluid of the flow stream 116 flows across as indicated by arrow 303.

In operation, light from the source 211 passes through the first sapphire plug 302 and through the fluid of the flow stream 116 where the light is attenuated prior to passing through the second sapphire plug 304. Unique absorption characteristics of the various constituents of the flow stream 116 cause at least some of the attenuation. The collimator 206 adjacent the second sapphire plug 304 focuses and concentrates the attenuated light into optical outputs 209 via the common connector 208. The optical outputs 209 typically include a multitude of optical fibers that are divided into groups 209a-d. Utilizing one type of standard connector, eighty-four fibers pack within the common connector 208 such that each of the four groups 209a-d comprise a total of twenty one fibers. However, the exact number of fibers and/or groups formed varies for other embodiments.

As illustrated in FIG. 3A by end view 207, the fibers within each of the groups 209a-d may be arranged to avoid sampling at discrete zones which may be affected by inconsistency of the source 211 and/or isolated variations within the flow stream 116. Specifically, each individual fiber receives light transmitted across a discrete light path through the fluid that is different from a light path of adjacent fibers. The end view 207 schematically illustrates fiber ends A, B, C, D corresponding to groups 209a, 209b, 209c, 209d, respectively, and arranged such that each quadrant of the end view 207 includes fibers from all groups 209a-d. For example, one fiber of the group 209a receives light passing through a path on the left side of the sampling region 204 while another fiber of the group 209a receives light passing through a path on the right side of the sampling region 204 such that the combined light from both fibers is detected. Accordingly, this arrangement may reduce errors caused by making a measurement at only one discrete location by effectively averaging the light received from all fibers within the group 209a.

Each of the four groups 209a-d connects to a respective housing 310 of one of the infrared filters 308 via a connector 306 such as an SMA connector. Each of the infrared filters 308 includes the housing 310, a narrow band pass filter 311 and a photo diode 313. The photo diode 313 produces an electrical signal proportional to the light received from a respective one of the groups 209a-d of the optical outputs 209 after passing through a respective one of the filters 311. Preferably, a logamp circuit (not shown) measures the electrical signals to give up to five decades of range. Each of the filters 311 filters all but a desired narrow band of infrared radiation. Since each of the filters 311 discriminate for a selected wavelength band that is unique to that filter, each of the groups 209a-d represent a different channel that provides a total attenuation signal 314 indicative of the total attenuation of the light at the wavelengths of that particular filter. Thus, the signals 314a-d from the four channels represent transmitted radiation at multiple different desired wavelength bands.

If only one wavelength is interrogated without comparison to other wavelengths, absorbance based attenuation associated with that one wavelength cannot be readily distinguished from other non-absorbance based attenuation that can introduce errors in an absorbance measurement. However, using multiple simultaneous wavelength measurements provided by the signals 314a-d from the different channels enables non-wavelength dependent attenuation, such as attenuation caused by common forms of scattering, to be subtracted out of the measurements. An appropriate algorithm removes these non-absorbance background influences based on the fact that the non-wavelength dependent attenuation provides the same contribution at each wavelength and thence at each channel regardless of wavelength dependent absorbance. Thus, comparing the signals 314a-d from each channel at their unique wavelengths enables correction for non-wavelength dependent attenuation.

Additionally, selection of the filters 311 determines the respective wavelength for each of the multiple simultaneous wavelength measurements associated with the signals 314a-d from the different channels. Accordingly, the different channels enable monitoring of wavelengths at absorbent peaks of the constituents of the flow stream 116, such as water absorbent peaks in addition to oil absorbent peaks, based on the wavelengths filtered. To generally improve resolution, a minute change in the property being measured ideally creates a relatively large signal. Since the relationship between concentration and absorption is exponential rather than linear, large signal changes occur in response to small concentration changes of a substance when there is a low cut or fraction of the substance being measured based on attenuation of the signal from the channel(s) monitoring the wavelengths associated with an absorbent peak of that substance. In contrast, small signal changes occur in response to concentration changes of the substance when there is a high cut of the substance being measured by the same channel(s).

Accordingly, the different channels provide sensitivity for the meter across a full range of cuts of the substance within the flow, such as from 0.0% to 100% phase fraction of the substance. For example, channel(s) with wavelengths at water absorbent peaks provide increased sensitivity for low water fractions while channel(s) with wavelengths at oil absorbent peaks provide increased sensitivity for high water fractions. Thus, the channel(s) with the highest sensitivity can be selected for providing phase fraction results or averaged with the other channels prior to providing the results in order to contribute to the sensitivity of the meter.

Another benefit of the multiple simultaneous wavelength measurements provided by the signals 314a-d from the different channels includes the ability to accurately calibrate the meter 101 with a small amount of pure fluid. Thus, calibration of the meter 101 does not require a reference cut. Selection of wavelengths as disclosed herein for the channels reduces sensitivity to different types of oil in order to further simplify calibration. For example, oils which are light in color or even clear have an optimal absorbance peak around a wavelength of 1,750 nanometers, but black oils have stronger absorbance around a wavelength of 1,000 nanometers. If two of the four channels include filters at these wavelengths, then the algorithm can determine the optimal choice at the calibration stage rather than requiring a hardware change for different oil types.

Figure 4:
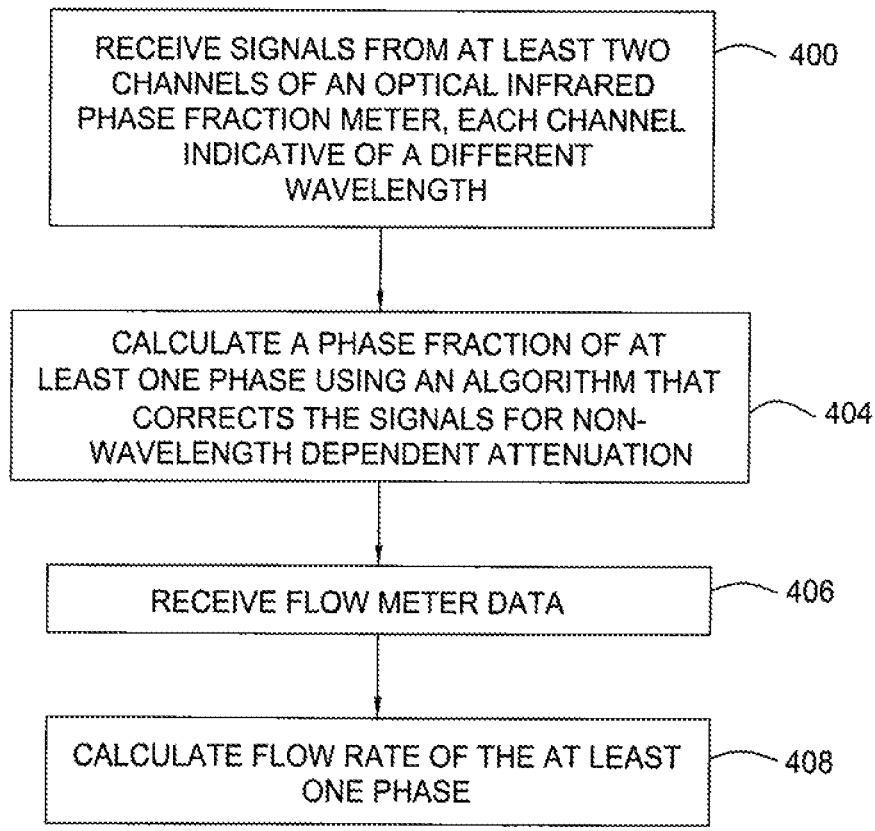
FIG. 4 is a flow chart of a flow processing technique performed by the phase fraction meter and a flow computer of FIG. 1.

FIG. 4 shows a flow chart of a flow processing technique performed by the phase fraction meter 101 and/or the flow computer 110 (shown in FIG. 1) after emitting infrared radiation into the flow stream 116. The processing begins at a step 400 where electronics receive signals 314a-b from at least two channels of the phase fraction meter 101. In a step 404, an algorithm calculates a phase fraction of at least one phase due in part on absorbance readings for "pure" substances made in a calibration step (not shown). The algorithm corrects the signals for non-wavelength dependent attenuation based on these influences effecting signals from each channel indiscriminately such that the non-wavelength dependent attenuation drops out in the solution of simultaneous equations. For example, a water cut of the flow stream 116 can be calculated by averaging or otherwise combining results from non-homogeneous linear equations calculated for each channel, wherein the equations include detector photocurrent values corrected for non-wavelength dependent attenuation, an absorption constant, and hardware constants. The following equation defines an exemplary equation that may be used for calculating the water cut ($C_W$) as measured by a single channel:

$$I_i = \beta(I_{oi})e^{-(a_{Oi}x_O + a_{Wi}x_W)} \quad (1)$$

$$x_O + x_W = 1 \quad (2)$$

where $I_i$ represents transmitted light at frequency band i, $\beta$ represents a frequency independent attenuation coefficient, $I_{Oi}$ represents incident light at frequency band i, $\alpha_{Oi}$ represents the absorption coefficient of the oil at frequency band i, $\alpha_{Wi}$ represents the absorption coefficient of the water at frequency band i, $x_O$ represents the fraction of the path length occupied by oil, and $x_W$ represents the fraction of the path length occupied by water. $x_W$ is equivalently the water cut "$C_W$" of the mixture. Equations 1 and 2 contain three unknowns, $x_O$, $x_W$, and $\beta$. A minimum of two frequencies are therefore required to solve for $C_W$:

$$C_W = x_W = \frac{\ln\left[\frac{I_2}{I_1}\right] - (a_{O1} - a_{O2})}{(a_{W1} - a_{W2}) - (a_{O1} - a_{O2})} \quad (3)$$

After receiving data from the flow meter 106 as indicated in a step 406, the flow computer calculates a flow rate of the at least one phase in a step 408.

Figure 5:
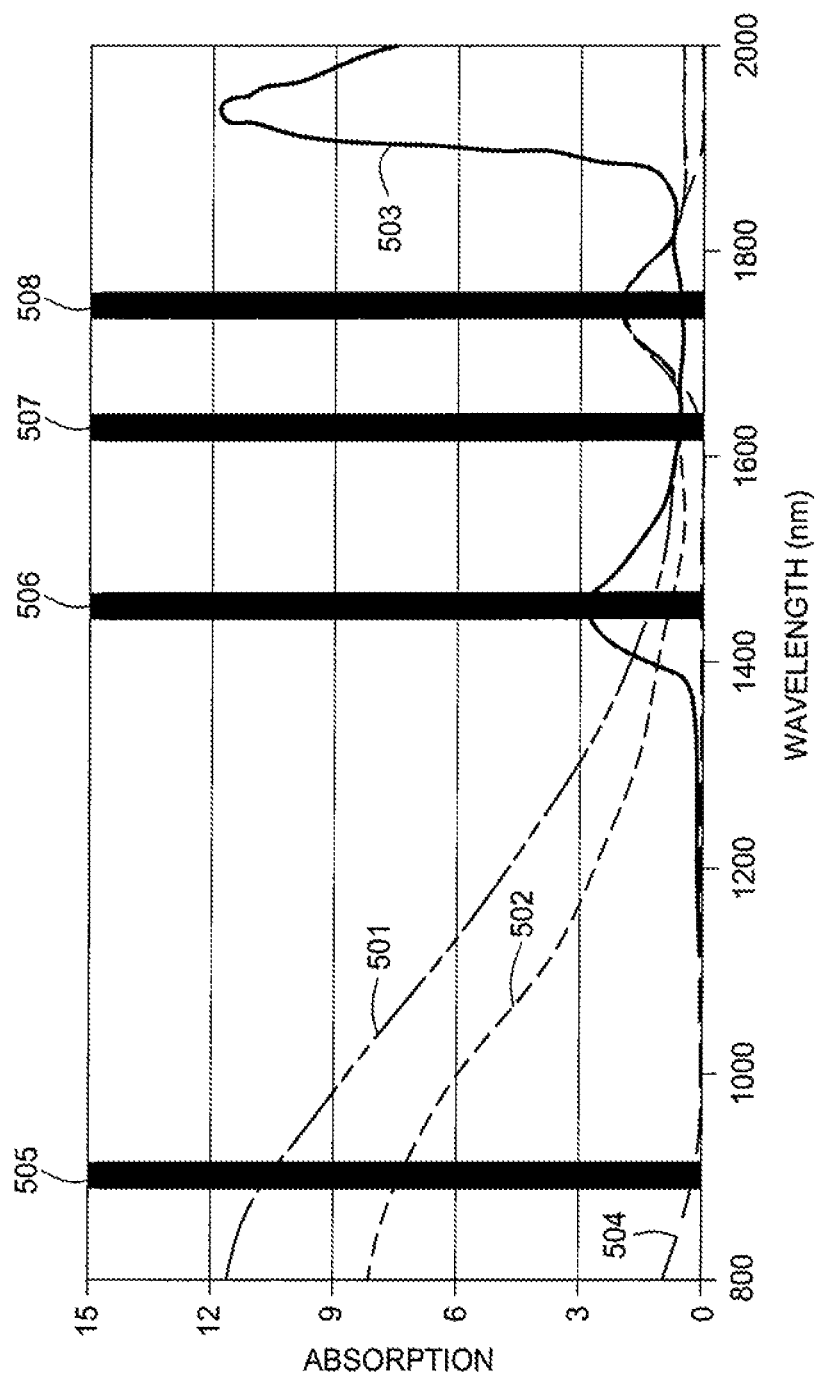
FIG. 5 is a graph illustrating absorption of two types of oil, water and condensate for an infrared region and wavelengths thereof selected for interrogation via channels of an infrared phase fraction meter.

FIG. 5 illustrates a graph of absorption verses wavelength for two types of oil indicated by curves 501, 502, water represented by curve 503 and condensate denoted by curve 504 for an infrared region. Gas provides relatively zero absorption and has accordingly been omitted from the graph. The graph shows four preferred wavelength bands 505-508 for filtering by the filters 311 in order to provide the four channels of the phase fraction meter 101. Other wavelength bands may be selected without departing from the scope of the invention. The phase fraction meter 101 essentially ignores salinity changes since typical salinity levels have negligible effect on water absorption over the spectral region of interest. Additionally, lack of significant absorption by gas makes the meter 101 substantially insensitive to free gas in the fluid stream 116.

In general, a first wavelength band 505 includes wavelengths within a range of approximately 900 nanometers (nm) to 1200 nm, for example about 950 nm, where there is an oil absorbent peak. A second wavelength band 506 includes wavelengths centered around 1450 nm where there is a water absorbent peak. A trough around 1650 nm provides another interrogation region where a third wavelength band 507 generally is centered. A fourth wavelength band 508 generally includes a peak centered about 1730 nm that is fundamentally associated with carbon-hydrogen bonds of the oil 501, 502 and the condensate 504. The substantial similarities and/or differences in the absorbance of the different phases at each of the bands 505-508 further enables their differentiation from one another with the phase fraction meter 101.

For some embodiments, the flow meter 106 may only provide a mass flow rate instead of a volumetric flow rate. In these embodiments, the phase fraction meter 101 measures the phase fraction as discussed above. The phase fractions of the oil and water are then multiplied by their respective known densities and summed to provide the density of the combined fluid since the gas density is minimal. The mass flow rate is then divided by this calculated density of the combined fluid to provide an accurate volumetric flow rate.

Different flow models or regimes may be useful for flow processing depending upon the particular application. For example, in an application, where gas and water travel at different velocities or where the oil travels in slugs through the pipe, a flow model can take these flow conditions into account.

The preferred embodiments use the broad band source and the filters to isolate wavelengths associated with the channels. However, other embodiments of the phase fraction meter include separate narrow band sources, tunable filters, and/or a single source that is swept for the desired wavelengths of the channels.

While the foregoing is directed to embodiments of the present invention, other and further embodiments of the invention may be devised without departing from the basic scope thereof, and the scope thereof is determined by the claims that follow.

What is claimed is:

1. An apparatus for computing volumetric flow rates of phases within a flow stream, comprising:
    a light source for emitting multiple wavelength bands of infrared radiation into a flow stream containing multiple phases, wherein the wavelength bands pass through certain phases and are absorbed by other phases and wherein at least one of the wavelength bands is disposed in a trough between two absorbent peaks;
    a detector for detecting fluctuations of the wavelength bands after the infrared radiation passes through a portion of the flow stream, wherein concentrations of the phases are determined based on the fluctuations of the wavelength bands;
    a flow meter wherein the flow meter measures a mass flow rate of the flow stream; and
    a flow computer wherein the flow computer calculates a mixture density of the flow stream based on densities and concentrations of the phases and calculates a flow rate of each phase based on the mixture density.

2. The apparatus of claim 1, further comprising a separator, wherein the separator is used to separate a combined stream into a gas stream and the flow stream.

3. The apparatus of claim 1, wherein the light source emits a first and second wavelength band corresponding to the water and oil phases respectively.

4. The apparatus of claim 3, wherein the first and second wavelength bands pass through a gas phase of the flow stream.

5. The apparatus of claim 3, wherein the first wavelength band is selected to be between about 900 nm and 1200 nm and the second wavelength band is selected to be about 1450 nm, and wherein a third wavelength band is selected to be about 1650 nm, and wherein a fourth wavelength band is selected to be about 1730 nm.

6. The apparatus of claim 1, wherein the detector simultaneously detects the fluctuation of the wavelength bands.

7. The apparatus of claim 1, wherein the detector comprises a plurality of optical fibers, wherein groups of optical fibers are routed to different outputs, and wherein each group of optical fibers consists of optical fibers dispersed within a sampling area.

8. The apparatus of claim 7, wherein each output is coupled to a narrow band filter and wherein each filter passes a specific wavelength band.

9. The apparatus of claim 1, wherein determining the concentration includes correcting a total fluctuation signal for non-wavelength dependent fluctuation, the correcting based on like fluctuation effects monitored at the wavelength bands.

10. The apparatus of claim 1, wherein the at least one of the wavelength bands disposed in the trough is at about 1650 nm.

11. An apparatus for computing volumetric flow rates of phases within a flow stream, comprising:
    a light source for emitting multiple wavelength bands of infrared radiation into a flow stream containing multiple phases, wherein the wavelength bands pass through certain phases and are absorbed by other phases;
    a detector for detecting fluctuations of the wavelength bands after the infrared radiation passes through a portion of the flow stream, wherein concentrations of the phases are determined based on the fluctuations of the wavelength bands, wherein the detector comprises a plurality of optical fibers, and wherein groups of optical fibers are routed to different outputs, and wherein each group of optical fibers consists of optical fibers dispersed within a sampling area;
    a flow meter wherein the flow meter measures a mass flow rate of the flow stream; and
    a flow computer wherein the flow computer calculates a mixture density of the flow stream based on densities and concentrations of the phases and calculates a flow rate of each phase based on the mixture density.

12. The apparatus of claim 11, wherein each output is coupled to a narrow band filter wherein each filter passes a specific wavelength band.

13. The apparatus of claim 11, wherein the light source emits a first and second wavelength band corresponding to the water and oil phases, respectively.

14. The apparatus of claim 13, wherein the first wavelength band is selected to be between about 900 nm and 1200 nm, wherein the second wavelength band is selected to be about 1450 nm, wherein a third wavelength band is selected to be about 1650 nm, and wherein a fourth wavelength band is selected to be about 1730 nm.

15. An apparatus for computing volumetric flow rates of phases within a flow stream, comprising:
    a light source for emitting multiple wavelength bands of infrared radiation into a flow stream containing multiple phases, wherein the wavelength bands pass through certain phases and are absorbed by other phases;

a detector for detecting fluctuations of the wavelength bands after the infrared radiation passes through a portion of the flow stream, wherein concentrations of the phases are determined based on the fluctuations of the wavelength bands;

a flow meter wherein the flow meter measures a mass flow rate of the flow stream; and a flow computer wherein the flow computer calculates a mixture density of the flow stream based on densities and concentrations of the phases and calculates a flow rate of each phase based on the mixture density, wherein calculating the concentration includes correcting a total fluctuation signal for non-wavelength dependent fluctuation, the correcting based on like fluctuation effects monitored at the wavelength bands.

16. The apparatus of claim 15, wherein the detector comprises a plurality of optical fibers, wherein groups of optical fibers are routed to different outputs, and wherein each group of optical fibers consists of optical fibers dispersed within a sampling area.

17. The apparatus of claim 16, wherein each output is coupled to a narrow band filter and wherein each filter passes a specific wavelength band.

18. The apparatus of claim 15, wherein the detector simultaneously detects the fluctuation of the wavelength bands.

19. The apparatus of claim 15, wherein the light source emits a first and second wavelength band corresponding to the water and oil phases, respectively.

20. The apparatus of claim 19, wherein the first wavelength band is selected to be between about 900 nm and 1200 nm, wherein the second wavelength band is selected to be about 1450 nm, wherein a third wavelength band is selected to be about 1650 nm, and wherein a fourth wavelength band is selected to be about 1730 nm.

* * * * *